(12) United States Patent
Brocchetta et al.

(10) Patent No.: US 6,479,681 B2
(45) Date of Patent: Nov. 12, 2002

(54) BILE ACID SALTS

(75) Inventors: Marino Brocchetta, Milan (IT); Chiara Gallotti, Milan (IT); Massimo Visigalli, Milan (IT); Pier Lucio Anelli, Milan (IT)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 09/934,603

(22) Filed: Aug. 23, 2001

(65) Prior Publication Data

US 2002/0019549 A1 Feb. 14, 2002

Related U.S. Application Data

(62) Division of application No. 09/449,998, filed on Nov. 26, 1999, now Pat. No. 6,307,074.

(30) Foreign Application Priority Data

Aug. 31, 1999 (IT) .......................................... MI99A1856

(51) Int. Cl.[7] .............................................. C07J 41/00
(52) U.S. Cl. ...................................... 552/520; 552/521
(58) Field of Search .......................................... 552/521

(56) References Cited

U.S. PATENT DOCUMENTS 5,486,626 A * 6/1996 Enhsen et al. ............... 552/521

OTHER PUBLICATIONS

Mar., J. Advanced Organic Chemistry, p–377–379, 1977.*

* cited by examiner

Primary Examiner—Sabiha Qazi
(74) Attorney, Agent, or Firm—Nixon & Vanderhye P.C.

(57) ABSTRACT

A process for the preparation of the compounds of general formula (I)

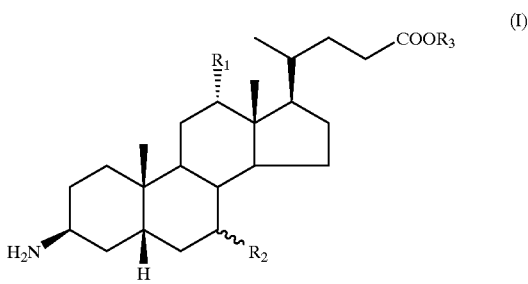

in which
$R_1$ is H or OH;
$R_2$ is H, α-OH, or β-OH; and
$R_3$ is a straight or branched $C_1$–$C_4$ alkyl group or a benzyl group,
comprising the reduction of compounds of formula (III)

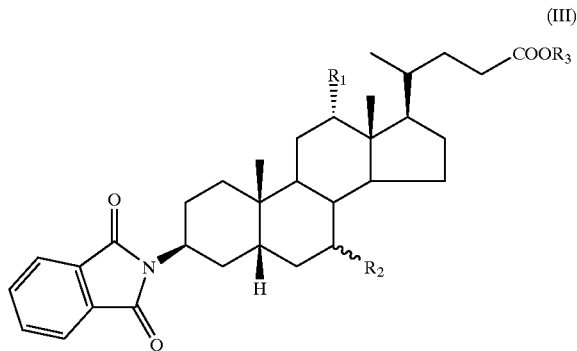

wherein $R_1$, $R_2$ and $R_3$ have the same meanings as in formula I, in the presence of sodium borohydride.

1 Claim, No Drawings

BILE ACID SALTS

This application is a division of application Ser. No. 09/449,998, filed Nov. 26, 1999, now U.S. Pat. No. 6,307,076, the entire content of which is hereby incorporated by reference in this application.

The present invention relates to a novel process for the preparation of bile acid derivatives in which an amino group is present at the 3β position.

The most important bile acids are represented in the following scheme 1:

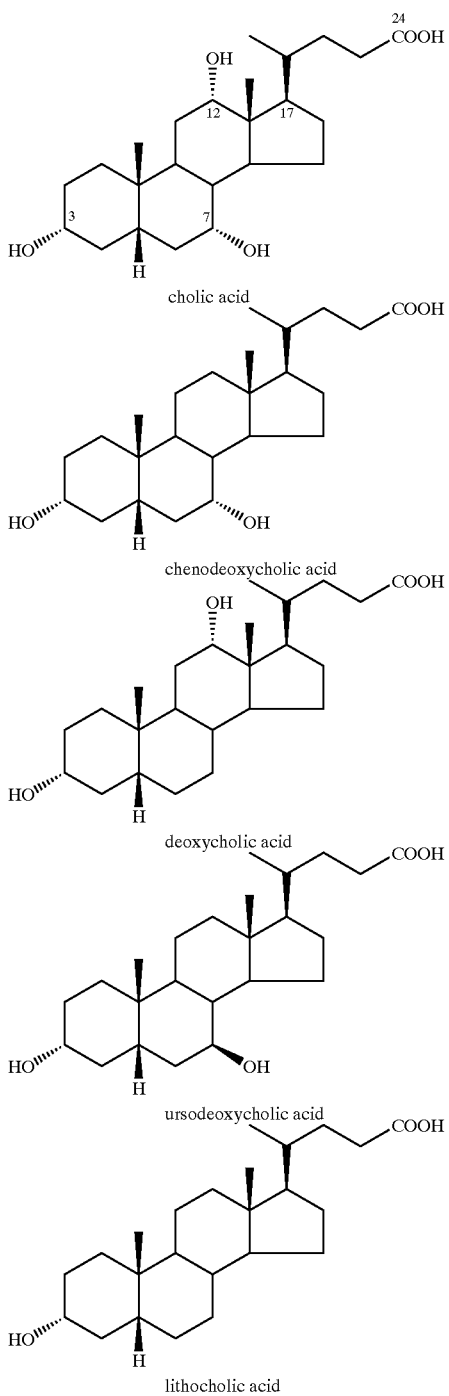

More particularly, the invention relates to a process for the preparation of compounds of formula (I) from compounds of formula (II):

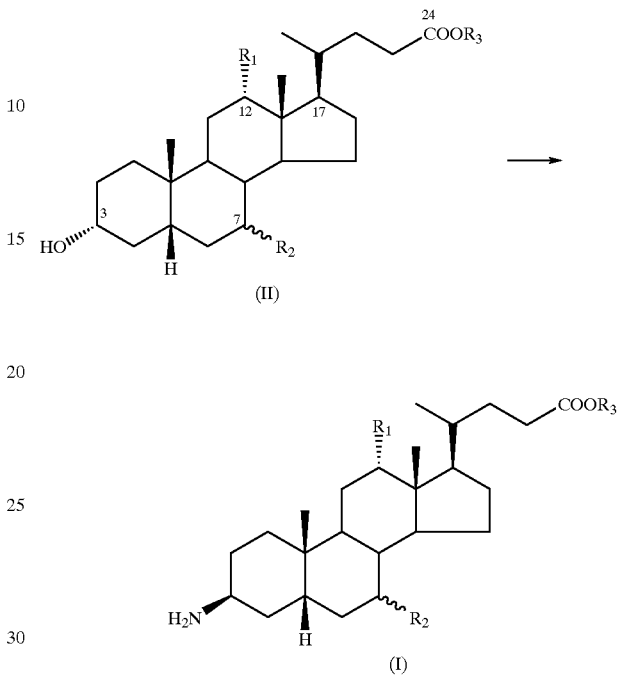

in which $R_1$ is H or OH;

$R_2$ is H, α-OH, or β-OH; and $R_3$ is a straight or branched $C_1$–$C_4$ alkyl group, or a benzyl group.

The compounds of general formula (I) are important intermediates for the preparation of compounds useful for a number of pharmaceutical applications. They are, for example, used for the preparation of inhibitors of bile acids intestinal absorption (see EP-A-0489423) or as carriers for active compounds in the enter-hepatic circulation (see EP-A-0417725).

Last, but not least, is the use thereof for the preparation of contrast agents for medical diagnosis using Magnetic Resonance, such as those described in WO-A-95/32741, resulting from the conjugation of a bile acid with a chelating agent, which are capable of chelating the ions of paramagnetic bi- and trivalent metals, in particular the gadolinium ion, or in the publication: Anelli P. L. et al., Acta Radiologica, 38, 125, 1997.

EP-A-614,908 discloses the preparation of the derivatives of general formula (I), comprising the following steps:

a) formation of phthalimido derivatives of general formula (III) by reacting compounds of general formula (II) with phthalimide;

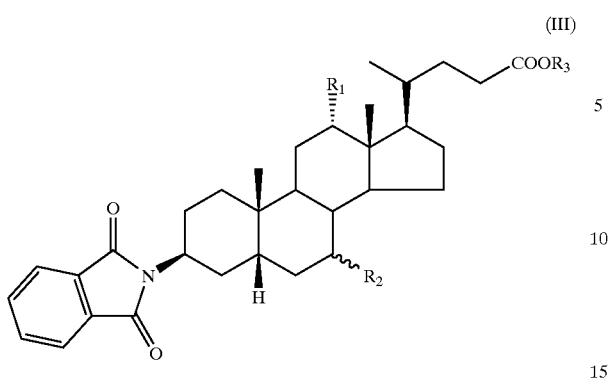

(III)

b) treatment of compounds of general formula (III) with hydrazine hydrate or phenylhydrazine;
c) subsequent treatment of the reaction products from step b) with mineral acids to form the addition salts, and
d) liberation from the salt to give the compounds of general formula (I).

As already widely discussed in EP-A-614,908, the formation of the phthalimido derivative is carried out by means of the well known Mitsunobu reaction (see Synthesis, 1, 1981; Org. React. Vol. 42, 335 (1992)), namely in the presence of a suitable phosphine and DEAD (diethylazodicarboxylate) or DIAD (diisopropylazodicarboxylate), in an organic solvent such as dioxane or tetrahydrofuran, at a temperature which ranges from 20 to 50° C. The Mitsunobu reaction yields the final products with inversion of configuration.

The process illustrated makes use of hydrazine hydrate or phenylhydrazine, particularly dangerous products due to their ascertained cancerogenicity.

It has now surprisingly been found that the reduction of the phthalimido group in the compounds of formula (III) can be advantageously carried out with sodium borohydride.

It is therefore the object of the present invention a process for the preparation of the compounds of general formula (I) comprising the reduction reaction of the compounds of general formula (III) in the presence of sodium borohydride, according to the following Scheme 2:

SCHEME 2

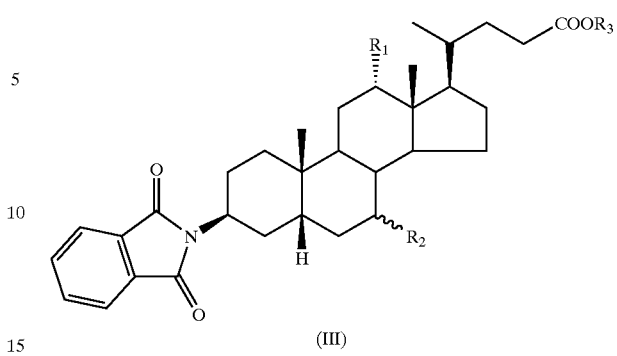

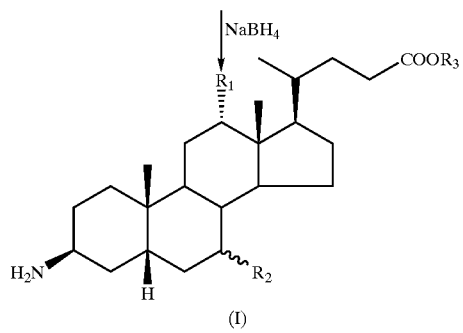

in which $R_1$ is H or OH;

$R_2$ is H, α-OH, or β-OH; and $R_3$ is a straight or branched $C_1$–$C_4$ alkyl group, or a benzyl group.

A further object of the present invention is the process for the preparation of the compounds of general formula (I) comprising the reduction of the compounds of general formula (III) in the presence of sodium borohydride, through formation of the novel compounds of general formula (IV), and subsequent deprotection by treating said compounds with acids, according to the following Scheme 3:

SCHEME 3

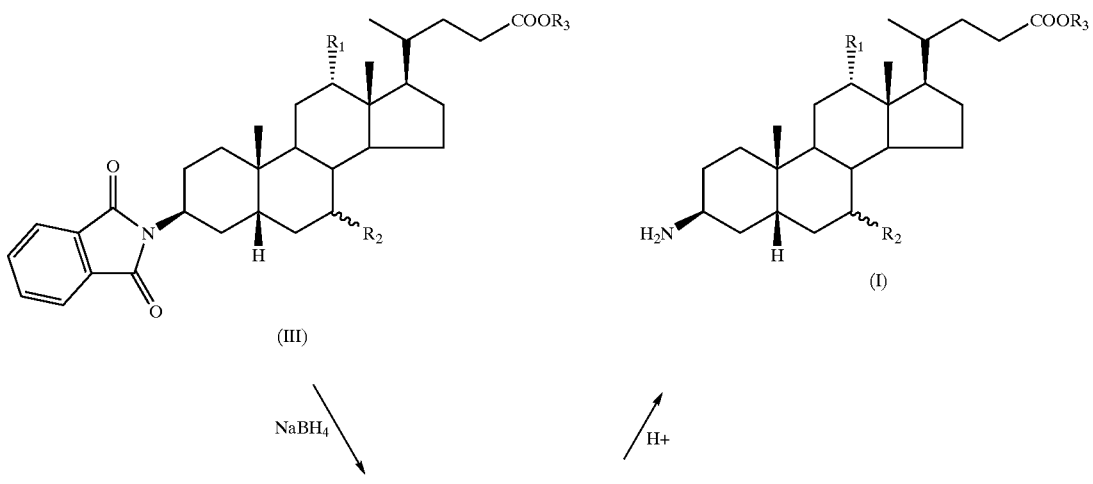

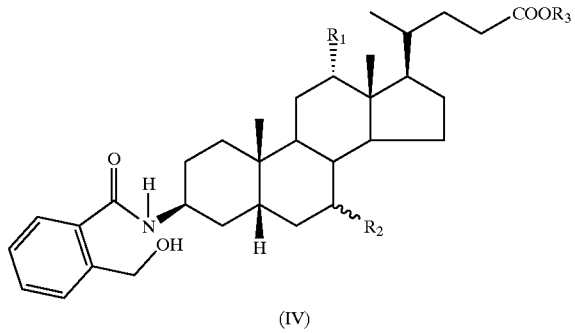

(IV)

in which $R_1$, $R_2$ and $R_3$ have the meanings defined above.

Compounds of general formula (IV) are novel, useful intermediates in the process according to Scheme 3 and their recovery will be described in the Experimental Section.

Particularly preferred is the process for the preparation of compounds of formula (Ia), according to Scheme 3, starting from compounds of formula (IIIa), which are derivatives of cholic or deoxycholic acid,

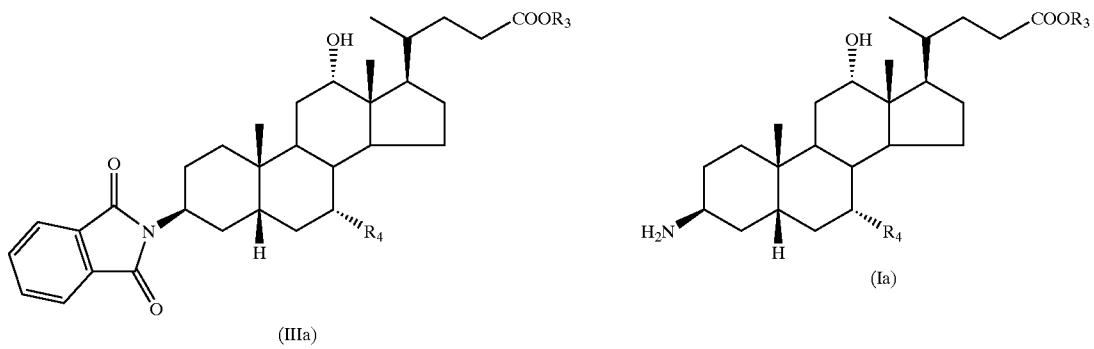

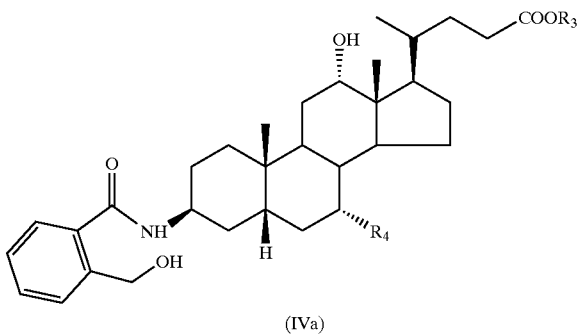

(IVa)

in which
$R_3$ has the meanings defined above and
$R_4$ can be a hydrogen atom or a hydroxy group.

A further object of the present invention is the process for the preparation of compounds of formula (Ib) according to Scheme 4, starting from compounds of formula (IIIb), which are deoxycholic acid derivatives,

SCHEME 4
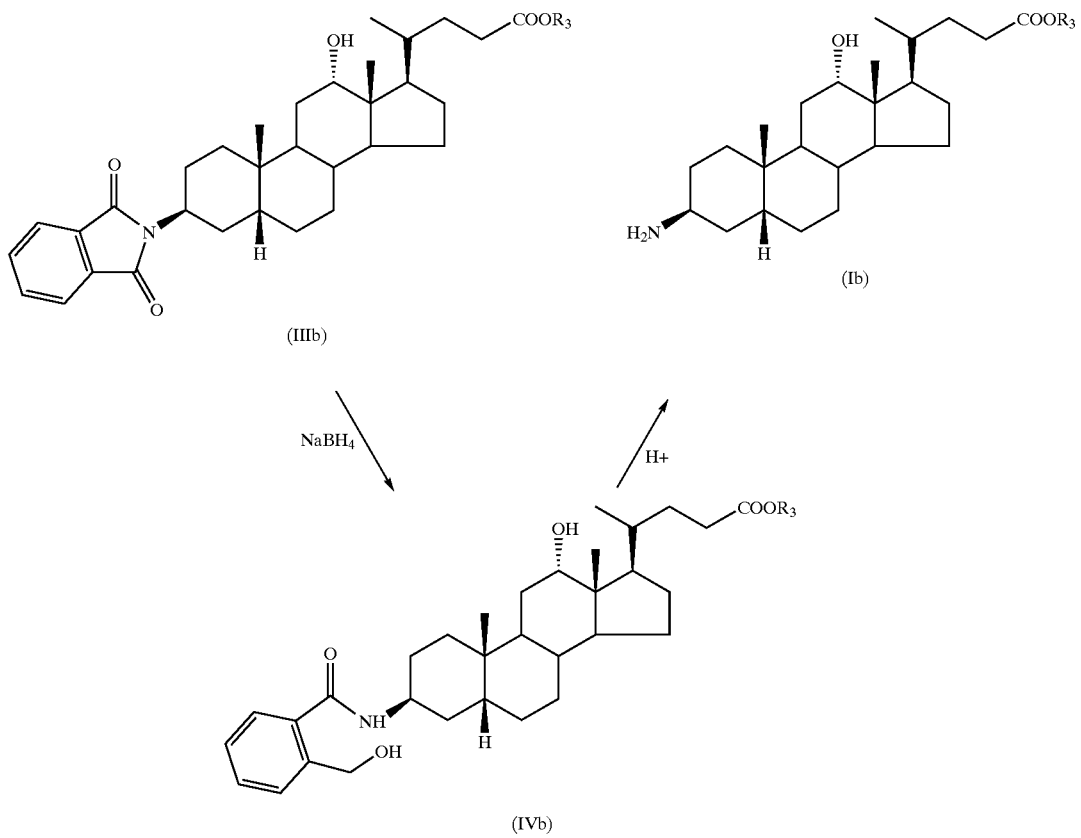
in which R₃ has the meanings defined above.
Particularly preferred is the process for the preparation of compound (Ic), according to Scheme 5, starting from compound (IIIc), a deoxycholic acid derivative,
SCHEME 5
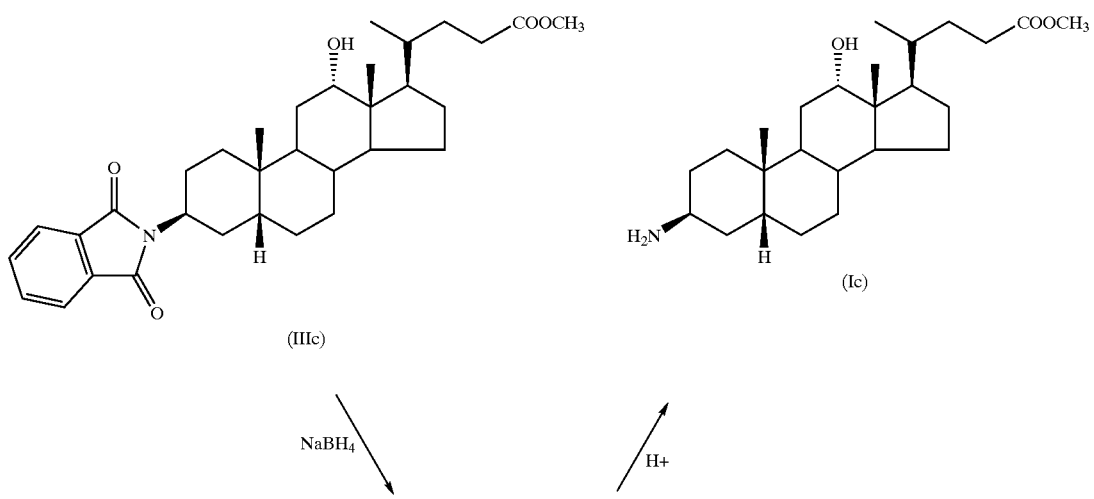

-continued

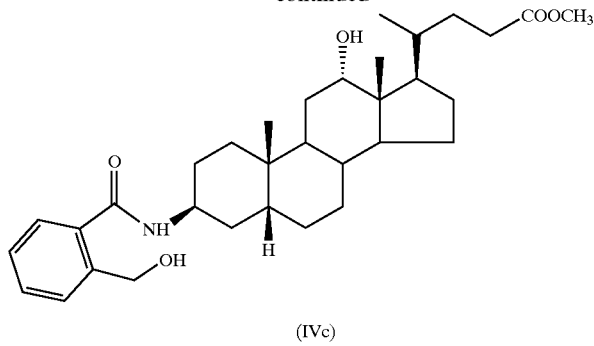

(IVc)

The compounds of formula (IIIc) and (IVc), (3β,5β,12α)-3-[1,3-dihydro-1,3-dioxo-2H-isoindol-2-yl)]-12-hydroxycholan-24-oic acid methyl ester and (3β,5β,12α)-12-hydroxy-3-[[(2-hydroxymethyl)benzoyl]amino]cholan-24-oic acid methyl ester, respectively, are novel and they are useful intermediates for the preparation of compound of formula (Ic), a deoxycholic acid derivative.

The compounds of formula (III) are synthesized according to the general procedure already described above and exemplified in EP-A-614,908.

Preferred reaction conditions comprise:

1) selection of a reaction temperature from 15 to 25° C., thus decreasing the amount of diisopropylazodicarboxylate to a small excess to the stoichiometric;
2) crystallization of phthalimido derivatives (III) from MeOH instead of 2-PrOH, thereby reducing the volume of the crystallization solvent by at least four times.

The reduction of phthalimido derivatives with $NaBH_4$ has never before been described in the field of the compounds of the present invention, but references exist in the literature, (T. W. Greene; P. G. M. Wuts "Protective groups in Organic Synthesis"; $3^{rd}$ Ed John Wiley and sons, New York, 1999), reporting the use of a large excess of this reducing agent (5–10 mol) to deprotect a phthalimido group.

The teaching contained in the most important paper [Osby, Tetrahedron Letters, Vol. 25, 2093 (1984)] i.e. the use of 2-PrOH/$H_2O$=6/1 as a reduction solvent proved to be definetly unsuitable for the process of the present invention. In fact, due to the poor solubility of compounds of formula (III), it was necessary to operate at temperatures around 40° C. and with a 2.5% maximum concentration which is of course industrially unacceptable.

On the other hand, Osby already evidenced that the proposed conditions were not particularly suitable to deprotect phthalimido groups from derivatives containing an ester function. Osby himself in fact observed that the deprotection of this group in said derivatives was accompanied by reduction and hydrolysis of the ester group with consequent decrease in reaction yields.

The Applicant found that when reducing the compounds of formula (III) under the Osby conditions, compounds of formula (I) were recovered in around 65% yields, but contaminated by remarkable amounts of by-products, mainly the product from the reduction of the ester group at 24- to alcohol. This phenomenon is still significant even when markedly reducing the $NaBH_4$ excess. In order to better understand the genesis of the by-products, the reaction carried out under the osby conditions was worked up at the end of the reduction with $NaBH_4$ and before the acid hydrolysis and the side-products recovered by silica chromatography had the formulae (V)–(VIII). These by-products are of course the precursors of the impurities evidenced in compounds of formula (I) and account for the low reaction yields.

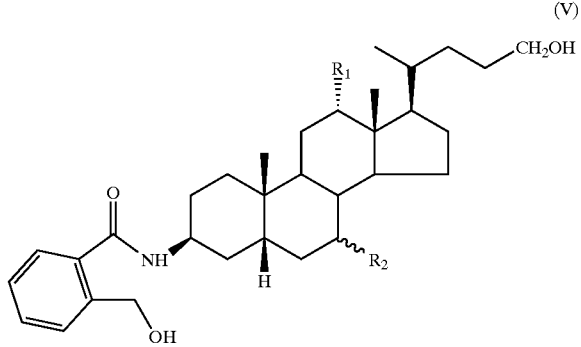

(V)

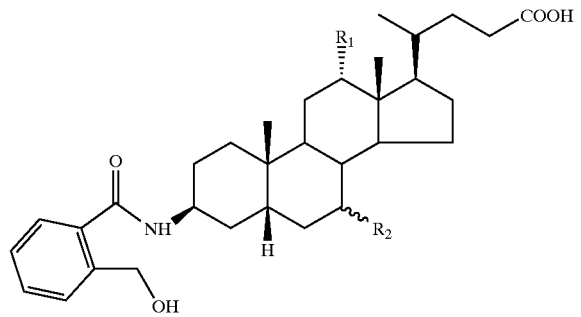

(VI)

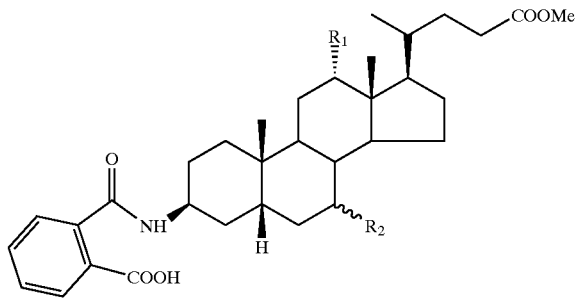

(VII)

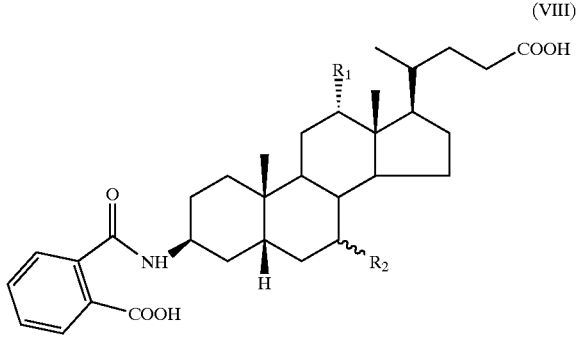

In the Experimental section the recovery and the characterization of the various intermediates, in particular in the case of deoxycholic acid, will be reported.

Compounds of formula (IV) are substantially inseparable from compounds (V) by crystallization from different solvents. Not even the conversion of compounds (IV) into the corresponding acids of formula (VI) allows the elimination of the by-products of formula (V).

It has surprisingly been found that using dipolar aprotic solvents such as DMA (dimethylacetamide), DMF (dimethylformamide), DMSO (dimethylsulfoxide), NMP (N-methyl-pyrrolidone), in place of an alcoholic solvent, such as isopropanol described by Osby, these problems could be overcome. Particularly preferred are dimethylacetamide and N-methylpyrrolidone.

Using said solvents the concentration of compounds (III) could be increased up to more than 10%, without increasing the amount of side-products.

Moreover, under the conditions of the present invention, the $NaBH_4$ excess could be decreased, compared with what reported above.

In particular, the molar equivalents of reducing agent can be lowered from a strong excess (about 5) to substantially stoichiometric values (1.2–0.85) to the substrate, without adversely affecting the reaction yields.

A further aspect of the present invention is the use, simultaneously with the dipolar aprotic. solvents, of a buffer solution at pH 7.5–9 which allows to control pH during the reaction. This allows to inhibit the hydrolysis of sensitive functions minimizing the formation of by-products (VI)–(VIII).

The compounds of formula (IV) are then transformed into those of formula (I) by treatment in dipolar aprotic or alcoholic solvent, optionally in mixture with water, and in the presence of a mineral or organic acid (such as acetic acid).

Particularly preferred is the use of HCl in methanol solution. The subsequent liberation of the free base from the salt is carried out by treatment of the solution in one of the above cited solvents with aqueous bases (such as NaOH, $Na_2CO_3$ ... ).

As already cited above, compounds of formula (I) are useful for the preparation of medicaments for decreasing cholesterol plasmatic levels, (EP-A-417,725 or EP-A-489,423) or of contrast agents for the nuclear magnetic resonance diagnosis, as described in WO-A-95/32741.

For the latter, the known synthesis comprised the transformation of compounds (II) into the corresponding compounds (I) by intermediate formation of the azide at the 3β position, according to Mitsunobu reaction, as represented in the following Scheme 6:

SCHEME 6

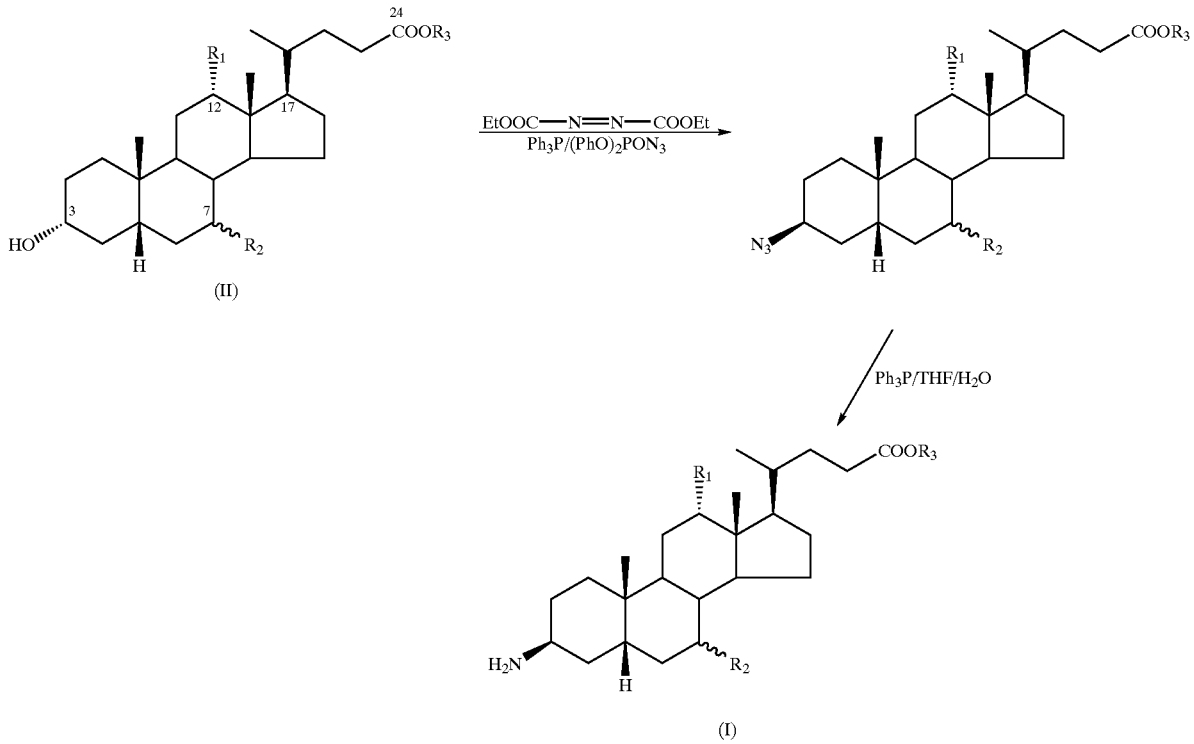

This Synthetic scheme is unsuitable for scaling-up, being azides potentially dangerous and the key reagent (diphenylphosphoryl azide) extremely expensive.

The present invention relates to a process for the preparation of chelating agents of general formula (IX), capable of chelating paramagnetic bi-trivalent metal ions, selected the group consisting of $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$ or $Mn^{(2+)}$,

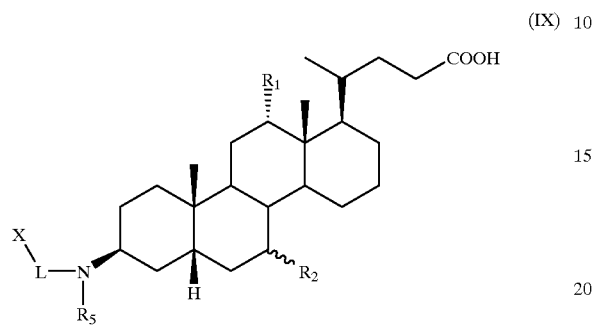

(IX)

in which $R_1$, and $R_2$ have the meanings defined above;

$R_5$ is a hydrogen atom or a $(C_1-C_5)$ alkyl group unsubstituted or substituted with a carboxylic group;

X is the residue of a polyaminocarboxylic ligand and of derivatives thereof, selected from the group consisting of: ethylenediaminotetraacetic acid (EDTA), diethylenetriaminopentaacetic acid (DTPA), 1,4,7,10-tetraazacyclododecane-1,4,7,10-tetraacetic acid (DOTA), 1,4,7,10-tetraazacyclododecane-1,4,7-triacetic acid (DO3A), [10-(2-hydroxypropyl)-4,7,10-tetraazacyclododecane-1,4,7-triacetic acid (HPDO3A), 4-carboxy-5,8,11-tris(carboxymethyl)-1-phenyl-2-oxa-5,8,11-triazatridecan-13-oic acid (BOPTA);

L is a residue of formula

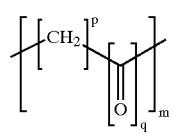

m is an integer from 1 to 10, wherein for values above 1, the values of p and q can differ in the monomeric units;

q is 0 or 1;

p can range from 0 to 10, p and q not being at the same time zero, said process comprising the following steps:

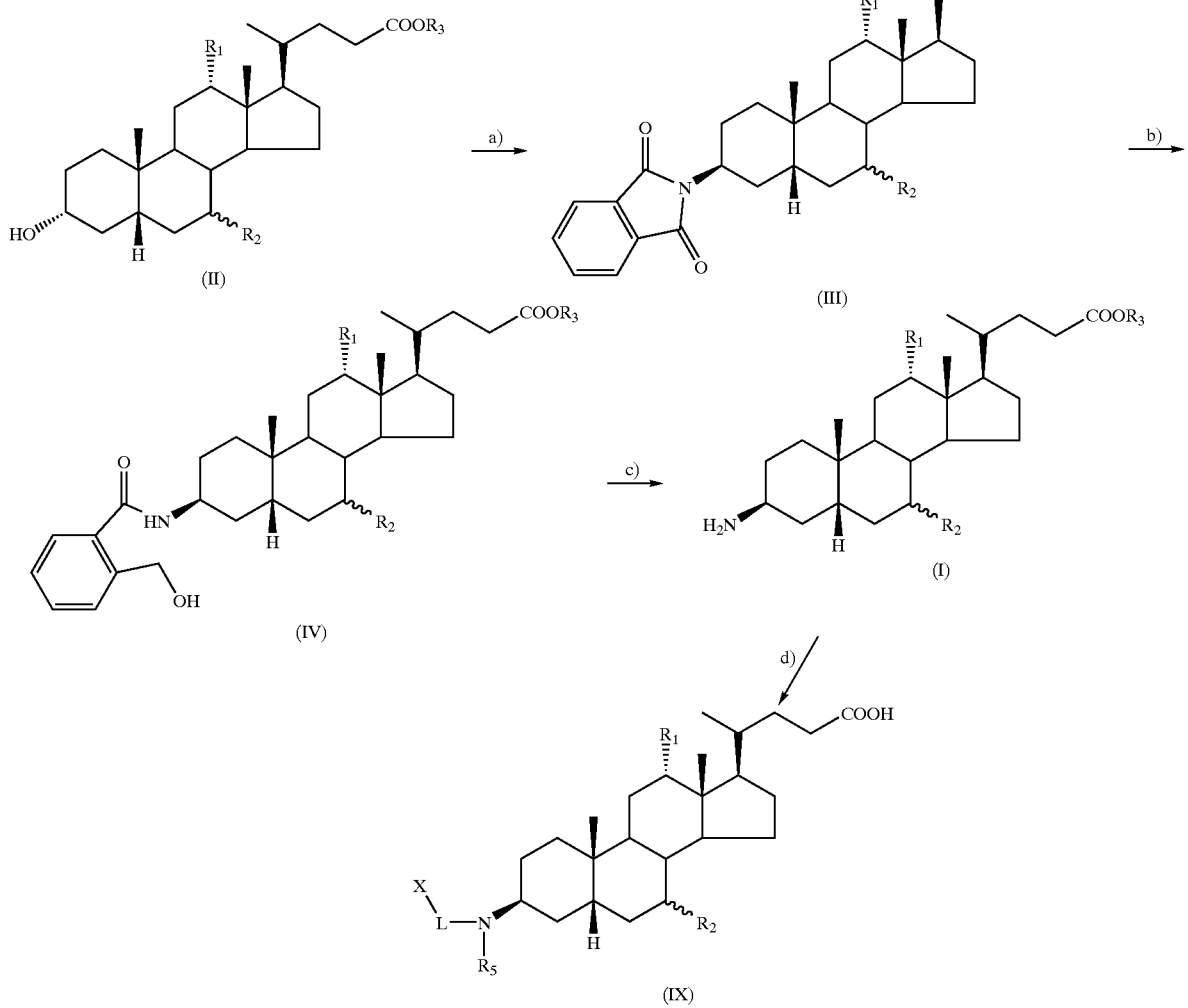

a) formation of compounds (III) starting from compounds (II) by reaction with phthalimide according to Mitsunobul's procedure, at temperatures ranging from 15 to 25° C., in the presence of an azodicarboxylate selected from DEAD (diethylazodicarboxylate) or DIAD (diisopropylazodicarboxylate) in amounts ranging from 1.1 to 1.3 molar equivalents, in a solvent selected from the group consisting of THF, dioxane, toluene and DMF;

b) reduction of compounds (III) with $NaBH_4$ to give compounds (IV);

c) acidic hydrolysis of compounds (IV) followed by neutralization to give compounds (I);

d) condensation of compounds (I) with the reactive residues of the polyaminocarboxylic ligands defined above.

Particularly preferred is the process for the preparation of compounds (IXa), which are cholic or deoxycholic acid derivatives, according to the following Scheme 7:

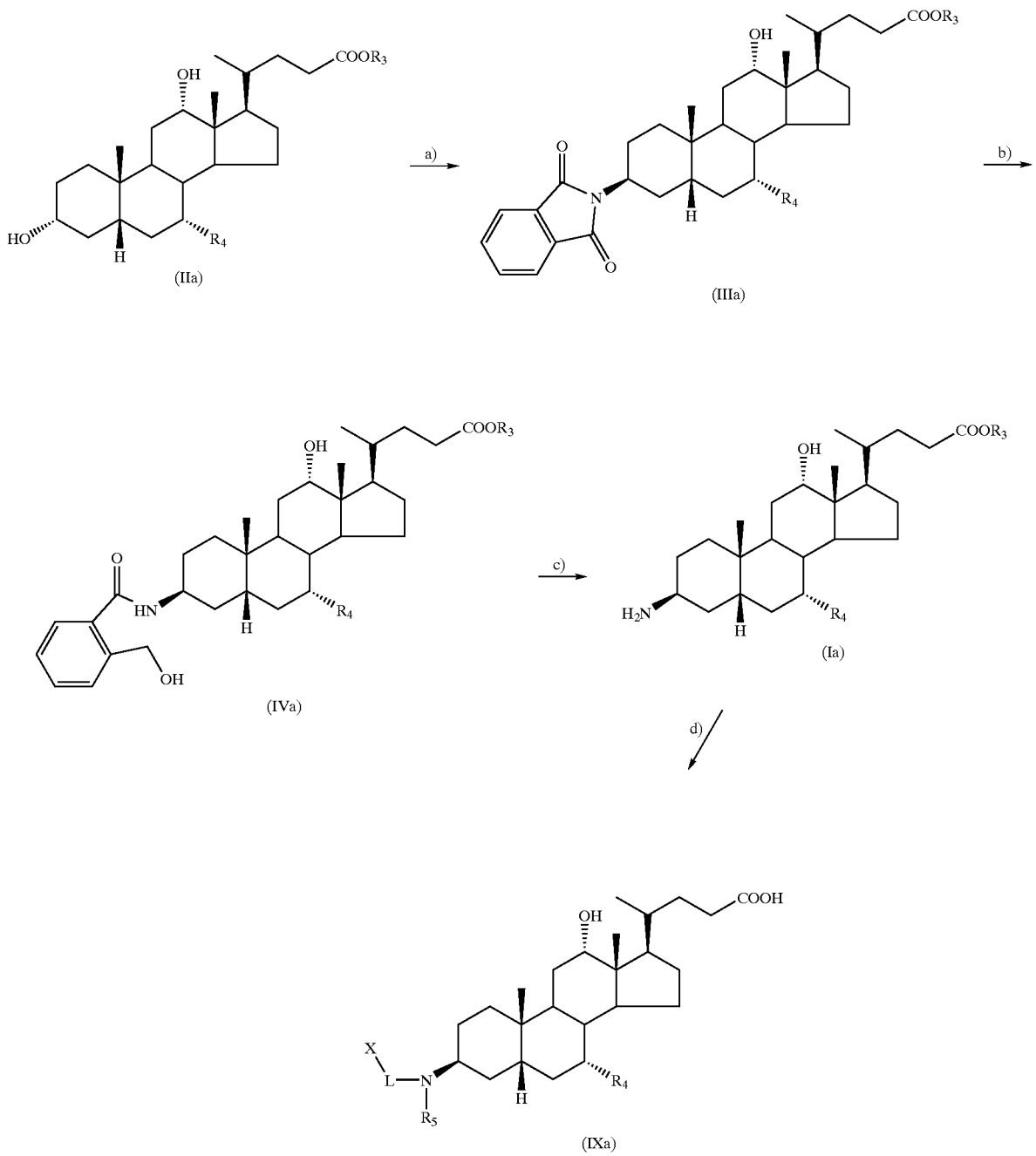

in which $R_3$, $R_4$ and $R_5$ have the meanings defined above.

Furthermore, particularly preferred is the process for the preparation of compounds (X), in which in formula (IXa) the residue X is DTPA substituted on the chain at the central position, $R_6$ can be a hydrogen atom or a carboxylic group and the L chain, $R_4$ and $R_5$ have the meanings defined above.

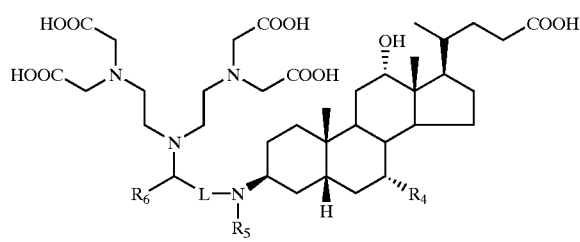

Particularly preferred is the process for the preparation of compounds (Xa)

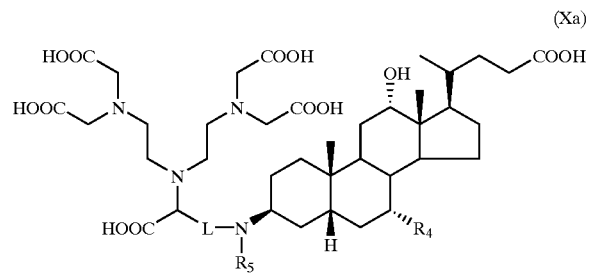

in which the L chain, $R_4$ and $R_5$ have the meanings defined above.

Furthermore, particularly preferred is the process for the preparation of the following novel compound, of general formula (Xa):

[3β(S),5β,12α,]-3-[[4-[bis[2-[bis(carboxymethyl)amino]ethyl]amino]-4-carboxy-1-oxobutyl]amino]-12-hydroxycholan-24-oic acid;

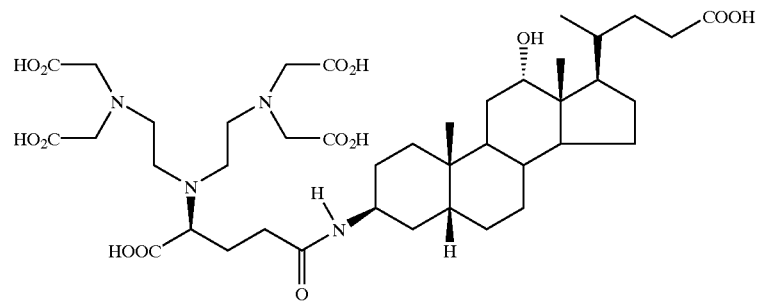

Other compounds belonging to this class, whose preparation has already been described in WO-A-95/32741, are the following:

[3β(S),5β,7α,12α]-3-[[4-[bis[2-[bis(carboxymethyl)amino]ethyl]-amino]-4-carboxy-1-oxobutyl]amino]-7,12-dihydroxycholan-24-oic acid;

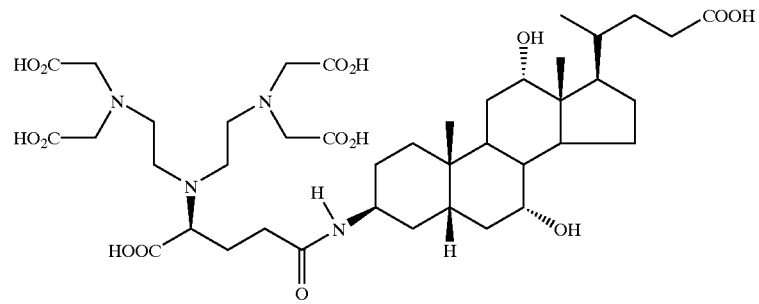

[3β(S),5β,7α,12α]-3-[[4-[[5-[bis[2-[bis(carboxymethyl)amino]-ethyl]amino]-5-carboxypentyl]amino]-1,4-dioxobutyl]amino]-7,12-dihydroxycholan-24-oic acid.

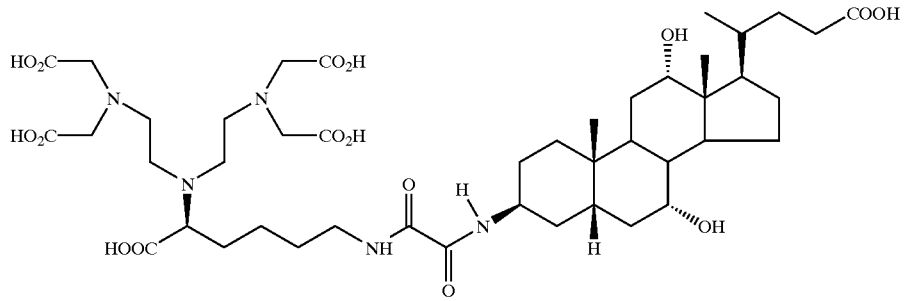

It is moreover preferred the process for the preparation of the following compounds of formula (Xb), in which in formula (X) $R_6$ is a hydrogen atom, and $R_4$, $R_5$ and L have the meanings defined above.

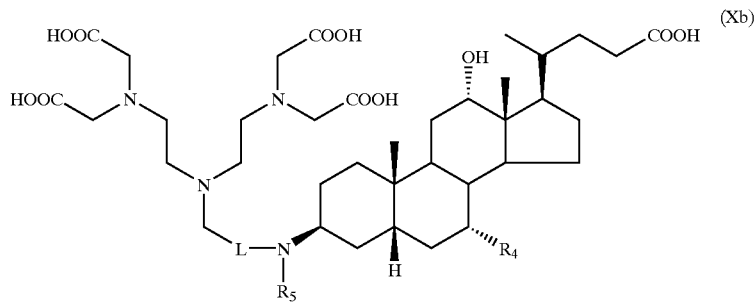

Also preferred is the process for the preparation of the following novel compound, belonging to the class of general formula (Xb):

(3β,5β,7α,12α)-3-[[[bis[2-[bis(carboxymethyl)amino]
ethyl]amino]acetyl]amino]-7,12-dihydroxycholan-24-oic
acid

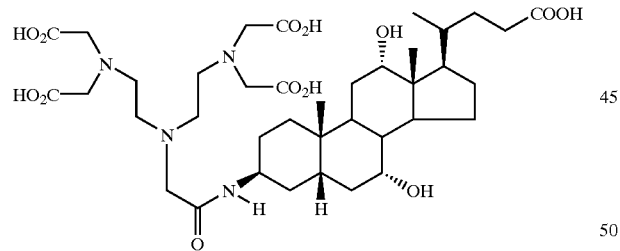

Other compounds belonging to this class, already described in WO-A-95/32741, are the following:

(3β,5β,7α,12α)-3-[[[[[bis[2-[bis(carboxymethyl)amino]
ethyl]amino]acetyl]amino]acetyl]amino]-7,12-dihydroxycholan-24-oic acid;

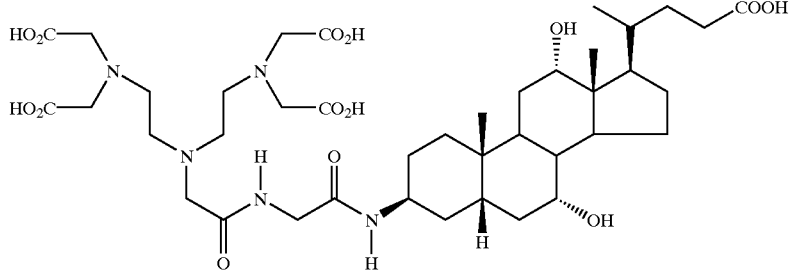

(3β,5β,7α,12α)-3-[[6-[[[bis[2-[bis(carboxymethyl)amino]ethyl]amino]acetyl]amino]-1-oxohexyl]amino]-7,12-dihydroxycholan-24-oic acid.

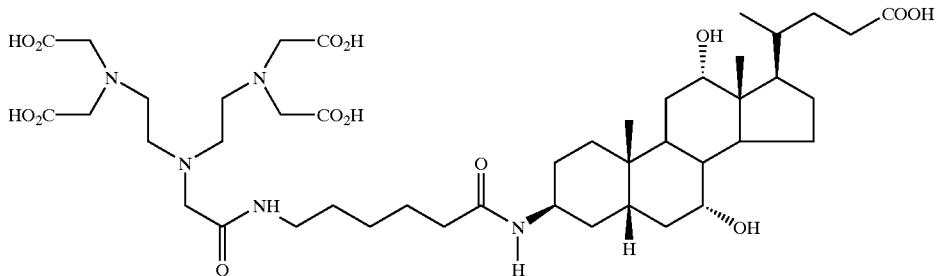

Particularly preferred is also the process for the preparation of compounds of formula (XI), in which in formula (IXa) the residue X derives from DTPA, and $R_4$, $R_5$ and L have the meanings defined above.

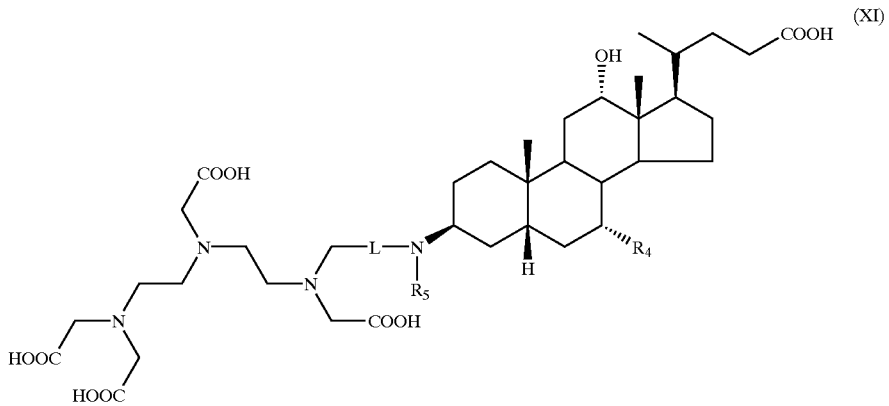

(XI)

Other compounds belonging to this class, whose preparation was already described in WO-A-95/32741, are the following:

(3β,5β,7α,12α)-3-[[N-[N-[2-[[2-[bis(carboxymethyl)amino]ethyl]-(carboxymethyl)amino]ethyl]-N-(carboxymethyl)glycyl]glycyl]amino]-7,12-dihydroxycholan-24-oic acid;

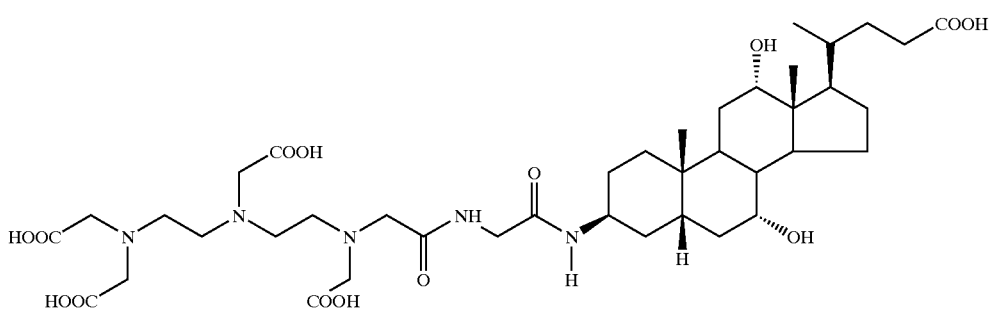

18-[[(3β,5β,7α,12α)-23-carboxy-7,12-dihydroxy-24-norcholan-3-yl]amino]-3,6,9-tris(carboxymethyl)-11,18-dioxo-3,6,9,12-tetraazaoctadecanoic acid.

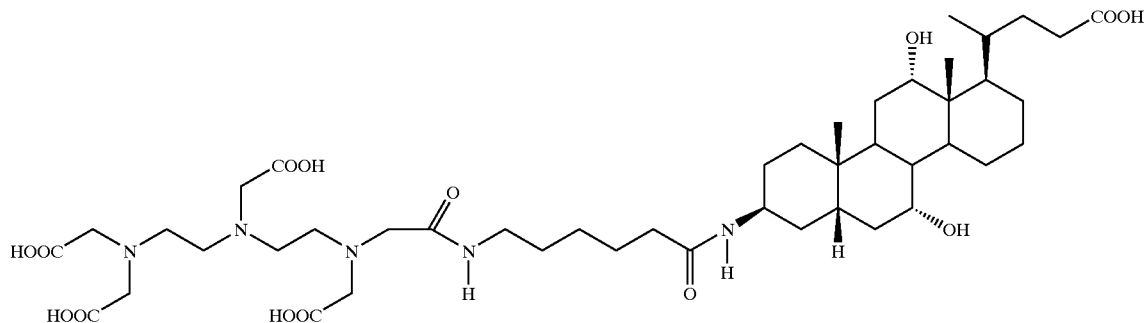

Particularly preferred is also the process for the preparation of the following compounds of formula (XII), in which in formula (IXa) the residue X is DOTA, and $R_4$, $R_5$ and L have the meanings defined above.

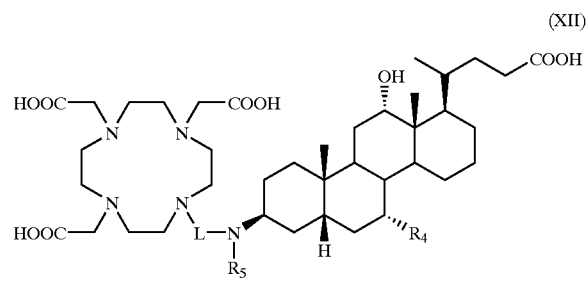

(XII)

Furthermore, preferred is the process for the preparation of compounds of formula (XIII), in which in formula (IXa) the residue X is EDTA, and $R_4$, $R_5$ and L have the meanings defined above.

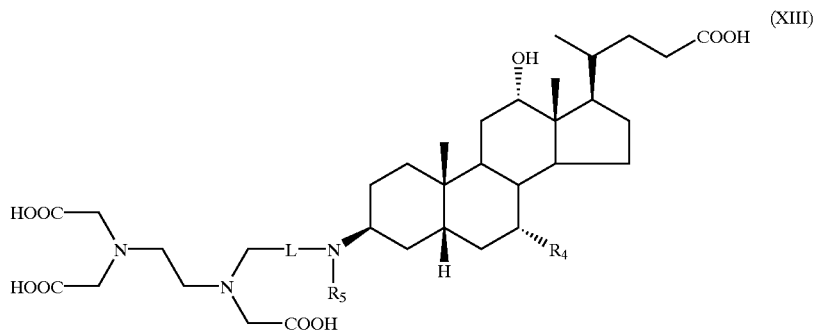

(XIII)

Particularly preferred is the process for the preparation of the following compounds of formula (XIII):
[3β(S) ,5β,7α,12α]-3-[[4-[[5-[[2-[bis(carboxymethyl)amino]ethyl]-(carboxymethyl)amino]-5-carboxypentyl]amino]-1,4-dioxobutyl]amino]-7,12-dihydoxycholan-24-oic acid

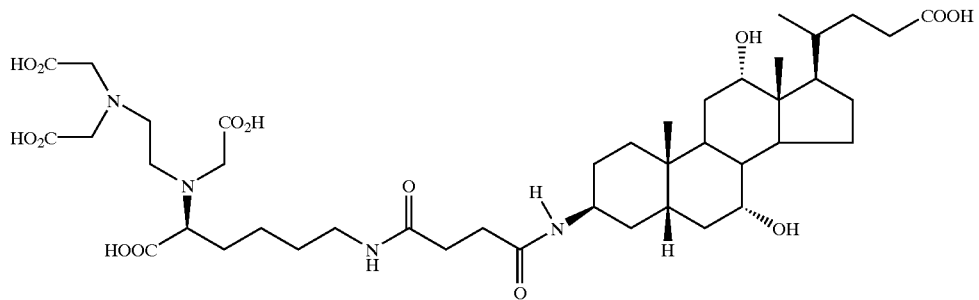
[3β(S),5β,12α]-3-[[4-[[2-[[bis(carboxymethyl)amino]ethyl]
(carboxymethyl)amino]-4-carboxy-1-oxobutyl]amino]-
12-hydroxycholan-24-oic acid
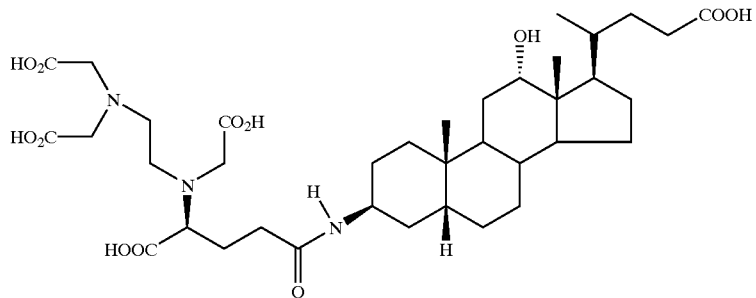
[3β(S),5β]-3-[[4-[[2-[[bis(carboxymethyl)amino]ethyl]
(carboxymethyl)amino]-4-carboxy-1-oxobutyl]amino]-
12-oxocholan-24-oic acid
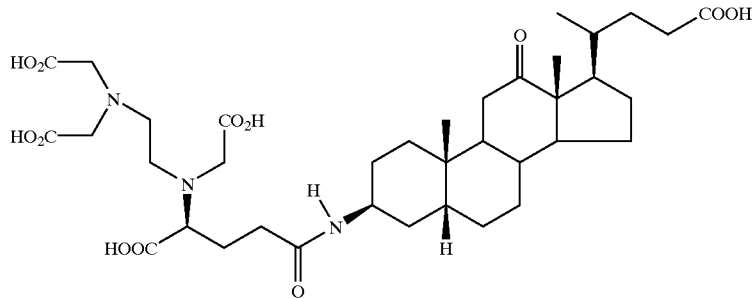
The experimental conditions used will be illustrated in detail in the Experimental Section.

EXPERIMENTAL SECTION

Example 1

(3β,5β,12α)-3-[1,3-Dihydro-1,3-dioxo-2H-isoindol-2-yl)]-12-hydroxycholan-24-oic acid methyl ester

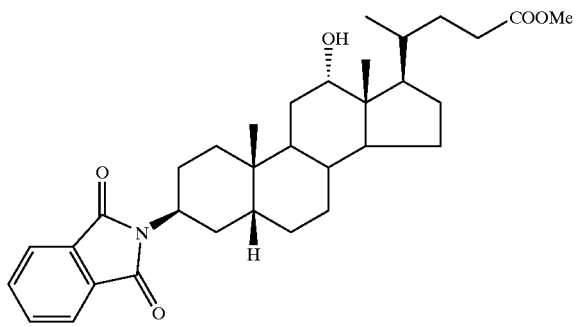

Phthalimide (202.8 g; 1.378 mol) is suspended in a solution of (3β,5β,12α)-3,12-dihydroxycolan-24-oic acid methyl ester (prepared as described in Steroids, vol. 37, 239) (511.9 g; 1.259 mol), and triphenylphosphine (372.7 g; 1.421 mol) in THF (1.5 L), then a solution of diisopropylazodicarboxylate (284.7 g; 1.408 mol) in THF (0.49 L) is dropped therein in 1.5 h, keeping the temperature at 15° C. The resulting solution is left at room temperature for 18 h. The solvent is distilled off and the oily residue is added with MeOH (3.2 L) and stirred for 20 h. The resulting crystalline product is filtered, washed with MeOH (1.4 L) and dried to give the desired product (481.3 g; 0.898 mol). Mother liquors and washings are concentrated to give a second crop of product (61.6 g; 0.114 mol)

Yield: 80%
m.p.: 160-162° C.
HPLC assay: 98.7%
Stationary phase: Lichrosorb RP-Select B 5 μm; column 250 × 4 mm Merck KGaA;
Temperature: 45° C.;
Mobile phase: gradient elution
A = 0.017M $H_3PO_4$ in water
B = $CH_3CN$ Gradient:

| min | % A | % B |
|---|---|---|
| 0 | 82 | 18 |
| 30 | 15 | 85 |
| 45 | 15 | 85 |

Flow: 1 mL min$^{-1}$;
Detection (UV): 210 nm;

Elemental analysis

| | C | H | N |
|---|---|---|---|
| % calc.: | 73.99 | 8.47 | 2.61 |
| % found: | 73.96 | 8.51 | 2.62 |

TLC: silica gel plate 60F 254 Merck
Eluent: AcOEt/n-hexane = 4:6 Rf: 0.35
Detection: 2% Ce(SO$_4$).4 H$_2$O, 4.2% (NH$_4$)$_6$Mo$_7$O$_{24}$, 6% H$_2$SO$_4$ in water The $^1$H-NMR, $^{13}$C-NMR, IR and MS spectra are consistent with the indicated structure.

Example 2

Reduction of compounds of formula (III) according to a procedure similar to that described in Osby, Tetrahedron Letters, Vol. 25, 2093 (1984).

(3β,5β,12α,)-3-Amino-12-hydroxycholan-24-oic acid methyl ester

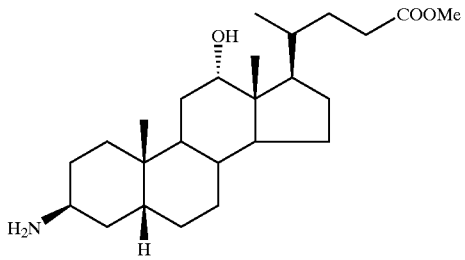

The compound prepared in Example 1 (75 g; 0.14 mol) is dissolved in 2-PrOH (2.5 L) at 75° C. The solution is vigorously stirred and cooled to 50° C., then added with H$_2$O (430 mL) to obtain a suspension which is added with solid NaBH$_4$ (26.5 g; 0.70 mol) in portions during 30 min. The reaction mixture is stirred at 40° C. for 2.5 h. CH$_3$COOH is carefully added to pH 4.5–5 and the mixture is heated at 80° C. for 24 h, keeping pH 4.5–5 by repeated additions of CH$_3$COOH. After cooling to room temperature and evaporation of the solvent, a residue is obtained which is dissolved in water (1 L). The solution is alkalinized to pH 10 with 2M NaOH to obtain a precipitate which is stirred for 1 h, then filtered, washed with water and dried.

Crystallization from acetonitrile (1.2 L) yields the desired product (36.9 g; 0.091 mol)

Yield: 65 %
HPLC assay: 87%
Stationary phase: Lichrosorb RP-Select B 5 μm; column 250 × 4 mm Merck KGaA;
Temperature: 45° C.;
Mobile phase: gradient elution
A = 0.01M sodium pentanesulfonate in water buffered to pH 2.5 with H$_2$SO$_4$
B = CH$_3$CN Gradient:

| min | % A | % B |
|---|---|---|
| 0 | 82 | 18 |
| 30 | 15 | 85 |
| 45 | 15 | 85 |

Flow: 1 mL min$^{-1}$;
Detection (UV): 210 nm;

Silica gel chromatography of the crude compound gave the main by-product (2.5 g) which was:

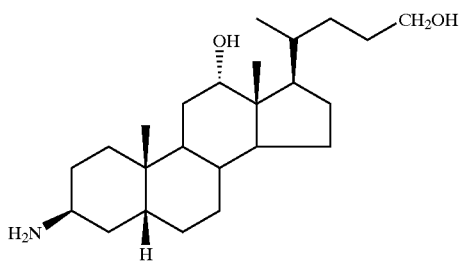

m.p.: 174–175° C.

Elemental analysis

| | C | H | N |
|---|---|---|---|
| % calc.: | 76.34 | 11.48 | 3.71 |
| % found: | 76.18 | 11.65 | 3.52 |

The ¹H-NMR, ¹³C-NMR, IR and MS spectra are consistent with the indicated structure.

In another reaction carried out under the above described conditions, at the end of the reduction the NaBH₄ excess was destroyed with acetic acid and the reaction mixture (about neutral pH) was evaporated and taken up with water to obtain a crude which was purified by silica gel chromatography. Together with the expected compound (IVb) (see EXAMPLE 3) remarkable amounts of the by-products, reported hereinbelow together with their analytical characterization, were recovered. This widely accounts for the low recovery yield of compound (Ib) after hydrolysis with acetic acid at 80° C.

N-[(3β,5β,12α)-12,24-Dihydroxycholan-3-yl]-2-(hydroxymethyl)benzamide

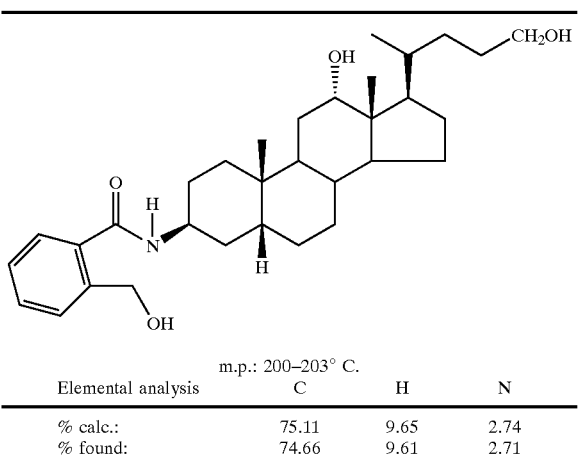

m.p.: 200–203° C.

| Elemental analysis | C | H | N |
|---|---|---|---|
| % calc.: | 75.11 | 9.65 | 2.74 |
| % found: | 74.66 | 9.61 | 2.71 |

(3β,5β,12α)-12-Hydroxy-3-[[2-(hydroxymethyl)benzoyl]amino]cholan-24-oic acid

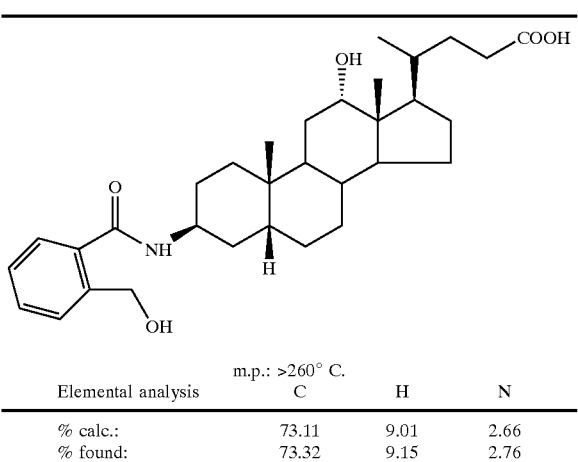

m.p.: >260° C.

| Elemental analysis | C | H | N |
|---|---|---|---|
| % calc.: | 73.11 | 9.01 | 2.66 |
| % found: | 73.32 | 9.15 | 2.76 |

N-[(3β,5β,12α)-12-Hydroxy-24-methoxy-24-oxocholan-3-yl]-2-(hydroxymethyl)benzamide

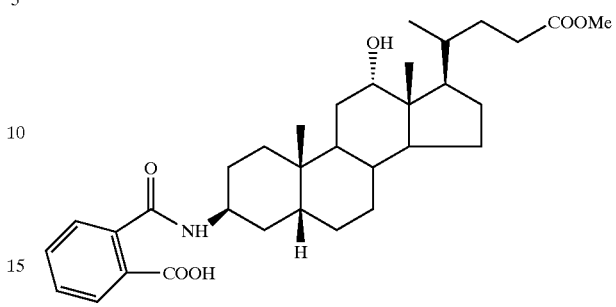

The product was characterized as ammonium salt m.p.: 156–162° C.

| Elemental analysis | C | H | N |
|---|---|---|---|
| % calc.: | 69.44 | 8.83 | 4.91 |
| % found: | 69.27 | 8.89 | 4.82 |

(3β,5β,12α)-12-Hydroxy-3-[[2-carboxybenzoyl]amino]cholan-24-oic acid

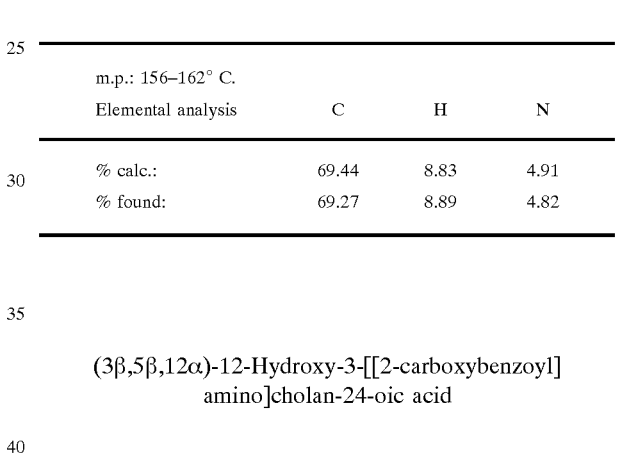

m.p. 193–196° C.

| Elemental analysis | C | H | N |
|---|---|---|---|
| % calc.: | 71.48 | 8.06 | 2.60 |
| % found: | 71.18 | 8.25 | 2.55 |

The ¹H-NMR, ¹³C-NMR, IR and MS spectra are consistent with the indicated structure.

Example 3

(3β,5β,12α,)-12-Hydroxy-3-[[(2-hydroxymethyl)benzoyl]amino]cholan-24-oic acid methyl ester

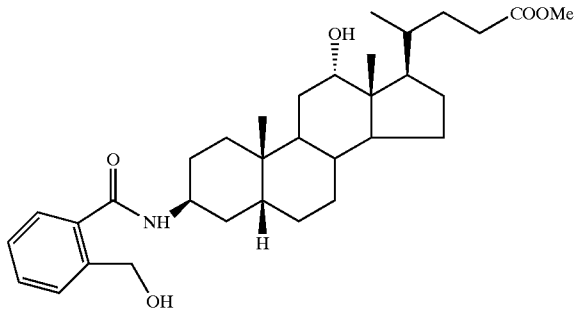

A solution of the compound prepared in Example 1 (225 g; 0.42 mol) in DMA (1.75 L), vigorously stirred at 34° C., is diluted with 2M buffer phosphate pH 8 (500 mL) obtaining a mixture at 43° C. Solid NaBH$_4$ (15.45 g; 0.408 mol) is added in 5 min and the suspension is stirred at 47–48° C. After 55 min an almost clear solution is obtained which is added with CH$_3$COOH to neutralize the hydride excess and adjust pH from 12.8 to about 8.

The mixture is poured into H$_2$O and stirred for 3 h, the precipitate is filtered and suspended in H$_2$O then stirred for 30 min. Finally, the precipitate is filtered, washed with H$_2$O and dried to give the desired product (224.6 g; 0.416 mol)

Yield: 99%
m.p. : 190.2–192.7° C.
HPLC assay: 93%

| Stationary phase: | Lichrosorb RP-Select B 5 μm; column 250 × 4 mm Merck KGaA; |
| --- | --- |
| Temperature: | 45° C.; |
| Mobile phase: | gradient elution<br>A = 0.017M H$_3$PO$_4$ in water<br>B = CH$_3$CN |

| Gradient: | min | % A | % B |
| --- | --- | --- | --- |
| | 0 | 82 | 18 |
| | 30 | 15 | 85 |
| | 45 | 15 | 85 |

| Flow: | 1 mL min$^{-1}$; |
| --- | --- |
| Detection (UV): | 210 nm; |
| Elemental analysis | C    H    N |

| | C | H | N |
| --- | --- | --- | --- |
| % calc.: | 73.43 | 9.15 | 2.60 |
| % found: | 73.43 | 9.19 | 2.56 |

| TLC: | silica gel plate 60F 254 Merck |
| --- | --- |
| Eluent: | AcOEt/n-hexane/MeOH = 5:5:1 Rf: 0.79 |
| Detection: | 2% Ce(SO$_4$).4 H$_2$O, 4.2% (NH$_4$)$_6$Mo$_7$O$_{24}$, 6% H$_2$SO$_4$ in water |

The $^1$H-NMR, $^{13}$C-NMR, IR and MS spectra are consistent with the indicated structure.

Example 4

(3β,5β,12α,)-3-Amino-12-hydroxycholan-24-oic acid methyl ester hydrochloride

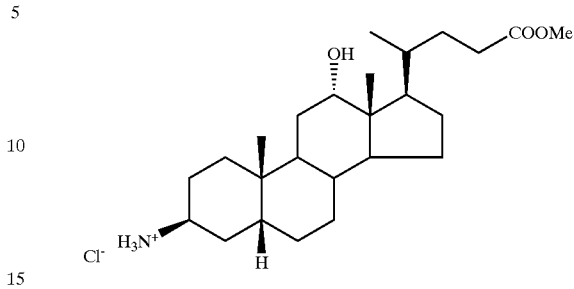

A suspension of the compound prepared in Example 3 (223.5 g; 0.414 mol) in MeOH (1.5 L) and 37% HCl (52 mL; 0.63 mol) is heated at 50° C under stirring. After about 1.5 h a solution is obtained and after a further 2 h, the 5 reaction is completed. The solvent is evaporated off and the residue is stirred at 60° C. for 2 h with CH$_3$CN. After 15 h at room temperature the precipitate is filtered, washed with CH$_3$CN and dried to give the desired product (183.3 g; 0.414 mol).

Yield: 100 %.
m.p. : > 250° C.
HPLC assay: 95%

| Stationary phase: | Lichrosorb RP-Select B 5 μm; column 250 × 4 mm Merck KGaA; |
| --- | --- |
| Temperature: | 45° C.; |
| Mobile phase: | gradient elution<br>A = 0.01M sodium pentanesulfonate in water buffered to pH 2.5 with H$_2$SO$_4$<br>B = CH$_3$CN |

| Gradient: | min | % A | % B |
| --- | --- | --- | --- |
| | 0 | 82 | 18 |
| | 30 | 15 | 85 |
| | 45 | 15 | 85 |

| Flow: | 1 mL min$^{-1}$; |
| --- | --- |
| Detection (UV): | 210 nm; |

Example 5

(3β,5β,12α,)-3-Amino-12-hydroxycholan-24-oic acid methyl ester

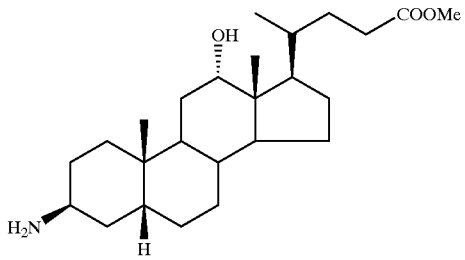

The compound prepared in Example 4 (89.5 g; 0.202 mol) is dissolved in MeOH (460 mL) at 55° C., then the solution is cooled to about 40° C. and poured, under strong stirring, into H$_2$O while adding solid Na$_2$CO$_3$ to keep pH 9.8. After stirring for 2 h, the suspension is filtered, the solid is suspended in H$_2$O and stirred for 2 h, filtered and washed with H$_2$O. After drying, the desired product is obtained (74.9 g; 0.185 mol).

Yield: 91%
m.p. : 155–155.5° C.
HPLC assay: 96.5%

| | |
|---|---|
| Stationary phase: | Lichrosorb RP-Select B 5 μm: column 250 × 4 mm Merck KGaA; |
| Temperature: | 45° C.; |
| Mobile phase: | gradient elution<br>A = 0.01M sodium pentanesulfonate in water buffered to pH 2.5 with $H_2SO_4$<br>B = $CH_3CN$ |

| Gradient: | min | % A | % B |
|---|---|---|---|
| | 0 | 82 | 18 |
| | 30 | 15 | 85 |
| | 45 | 15 | 85 |

| | |
|---|---|
| Flow: | 1 mL min$^{-1}$; |
| Detection (UV): | 210 nm; |
| GC assay: 96.3% | |
| Stationary phase: | PE 1 (OV 1) |
| Film thickness: | 0.25 μm |
| Column (WCOT): | 30 m × 0.32 mm |
| Starting temperature in the oven: | 255° C., after 5 min the temperature is increased by 0.6° C./min to reach 290° C. |
| Injector temperature: | 290° C. |
| Temperature FID: | 290° C. |

| Elemental analysis | C | H | N |
|---|---|---|---|
| % calc.: | 74.03 | 10.69 | 3.45 |
| % found: | 73.91 | 10.78 | 3.44 |

| | |
|---|---|
| TLC: | silica gel plate 60F 254 Merck |
| Eluent: | $CHCl_3$/MeOH/25% $NH_4OH$ = 6:2:0.5<br>Rf: 0.69 |
| Detection: | 2% $Ce(SO_4).4 H_2O$, 4.2% $(NH_4)_6Mo_7O_{24}$, 6% $H_2SO_4$ in water |

The $^1$H-NMR, $^{13}$C-NMR, IR and MS spectra are consistent with the indicated structure.

Compounds of formula (I), whose formulae and analytical data are reported hereinbelow, were prepared analogously:

| | m.p. (° C.) | Rf$^a$ |
|---|---|---|
| [structure: COOMe, OH, $H_2N$, H] | 164–166 | 0.48 |

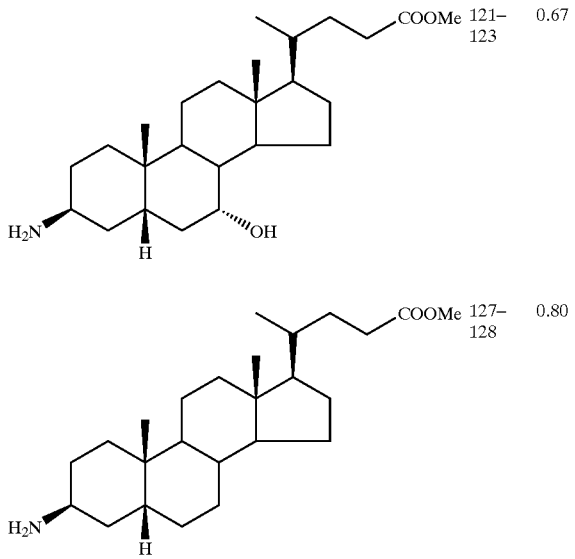

| | m.p. (° C.) | Rf$^a$ |
|---|---|---|
| [structure COOMe, $H_2N$, OH, H] | 121–123 | 0.67 |
| [structure COOMe, $H_2N$, H] | 127–128 | 0.80 |

$^a$ TLC: silica gel plate 60F 254 Merck
Eluent: $CHCl_3$/MeOH/25% $NH_4OH$ = 6:2:0.5
Detection: 2% $Ce(SO_4).4 H_2O$, 4.2% $(NH_4)_6Mo_7O_{24}$, 6% $H_2SO_4$ in water The $^1$H-NMR, $^{13}$C-NMR, IR and MS spectra as well as the elementary analysis are consistent with the indicated structure.

Example 6

[3β(S),5β,12α]-3-[[4-[Bis[2-[bis(carboxymethyl)amino]ethyl]-amino]-4-carboxy-1-oxobutyl]amino]-12-hydroxycholan-24-oic acid

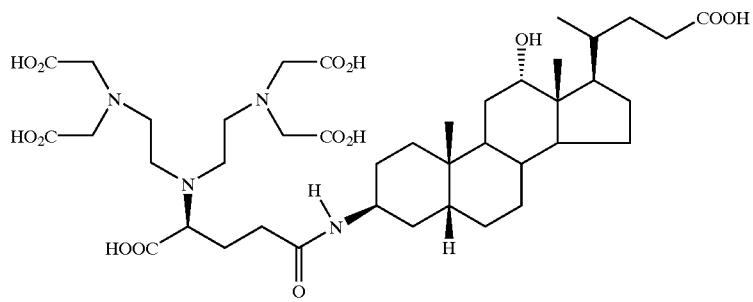

A) [(3β(S),5β,12α-3-[[4-[Bis[2-[bis[2-(1,1-dimethylethoxy)-2-oxoethyl]amino]ethyl]amino]-5-(1,1-dimethylethoxy)-1,5-dioxopentyl]amino]-12-hydroxycholan-24-oic acid methyl ester Triethylamine (2.23 g; 22 mmol) is added to a solution of 8.93 g of [3β,5β,12α[-3-amino-12-hydroxycholan-24-oic acid methyl ester (prepared in Example 5) (22 mmol), 16.41 g of N,N-bis[2-[bis[2-(1,1-dimethylethoxy)-2-oxoethyl]amino]ethyl]-L-glutamic acid (1,1-dimethylethyl) ester (prepared as described in WO-A-95/32741: example 15) (22 mmol) and 3.91 g of diethyl cyanophosphate (24 mmol) in 300 mL of DMF at 0° C. After 1.5 h at 0° C. and 18 h at room temperature, the reaction mixture is evaporated and the residue is dissolved in AcOEt. The solution is washed with a NaHCO$_3$ saturated solution and H$_2$O, dried (Na$_2$SO$_4$) and evaporated. The crude is purified by flash chromatography to give the desired product (20.67 g; 18.2 mmol).

Yield: 83%
$[\alpha]_D^{20}$ = −6.75 (c 2.0, CHCl$_3$)

| Elemental analysis | C | H | N |
|---|---|---|---|
| % calc.: | 65.69 | 9.60 | 4.94 |
| % found: | 66.54 | 9.95 | 4.99 |

TLC: Carrier: silica gel plate 60F 254 Merck

Eluent: n-hexane/EtOAc=1:1 R$_f$=0.09

Detection: Ce(SO$_4$)$_2$.4 H$_2$O (0.18%) and (NH$_4$)$_6$Mo$_7$O$_{24}$.4 H$_2$O (3.83%) in 10% H$_2$SO$_4$ The $^1$H-NMR, $^{13}$C-NMR, IR and MS spectra are consistent with the indicated structure.

B) [3β(S),5β,12α]-3-[[4-[Bis[2-[bis(carboxymethyl)amino]ethyl]amino]-4-carboxy-1-oxobutyl]amino]-12-hydroxycholan-24-oic acid The compound prepared at step A) (19.72 g; 17.4 mmol) is dissolved in 105 mL of CF$_3$CO$_2$H at room temperature. After 26 h the solution is evaporated and the residue is treated with H$_2$O; the solid is filtered, washed with H$_2$O and partially dried under vacuum. The resulting intermediate is dissolved in H$_2$O at pH 13 with 1M NaOH.

After 5 h at room temperature the solution is dropwise added with 0.5M HCl at pH 1.4. After 15 h at room temperature the precipitate is filtered, washed with H$_2$O and dried under vacuum to give a crude which is purified by chromatography on Amberlite(R) XAD 1600 resin to obtain the desired product (9.92 g; 11.8 mmol).

Yield: 68% m.p.: 184° C. (dec.)
Compleximetric titer (0.1M GdCl$_3$) : 99.3%
Acidic titer (0.1M NaOH): 99.8%
$[\alpha]_D^{20}$ (c 2.0; 1M NaOH)

| λ (nm) | 589 | 578 | 546 | 436 | 405 | 365 |
|---|---|---|---|---|---|---|
| [α] | +23.61 | +24.59 | +27.90 | +46.67 | +55.61 | +71.40 |

| Elemental analysis | C | H | N | |
|---|---|---|---|---|
| % calc.: | 58.70 | 7.93 | 6.68 | |
| % found: | 58.22 | 8.16 | 6.59 | H$_2$O 0.70% |

TLC: silica gel plate 60F 254 Merck

Eluent: CHCl$_3$/MeOH/NH$_4$OH 5:4:2
Rf = 0.13

Detection: Ce(SO$_4$)$_2$.4 H$_2$O (0.18%) and (NH$_4$)$_6$Mo$_7$O$_{24}$.4 H$_2$O (3.83%) in 10% H$_2$SO$_4$ The $^1$H-NMR, $^{13}$C-NMR, IR and MS spectra are consistent with the indicated structure.

Example 7

(3β,5β,7α,12α)-3-[[[Bis[2-[bis(carboxymethyl)amino]ethyl]amino]acetyl]amino]-7,12-dihydroxycholan-24-oic acid

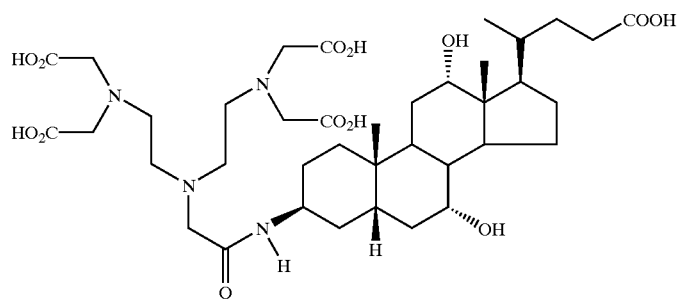

A) N-[[Bis[2-[bis[2-(1,1-dimethylethoxy-2-oxoethyl]amino]ethyl]amino]-acetyl]glycine 6.5 g of glycylglycine (49.3 mmol) are suspended in 100 mL of a 1:1=H$_2$O: EtOH mixture and dissolved at pH 10 with 10M NaOH (4.8 mL). N-(2-bromoethyl)-N[2-(1,1-dimethylethoxy)-2-oxoethyl]glycine-1,1-dimethylethyl ester (42 g; 110.9 mmol) in 40 mL of EtOH is dropped in 2 h keeping pH at 10.5 with 10M NaOH (5.8 mL). The solution quickly turns to an emulsion, which is dissolved after 2.5 h by addition of 10M NaOH. After 22 h the solvent is evaporated off, the residue is diluted with water and extracted with CH$_2$Cl$_2$. The organic phase is washed with $H_2O$, dried and evaporated, to give a residue which is purified by flash chromatography. The residue is dissolved in water, pH is adjusted to 4.5 by addition of 1M HCl and the solution is extracted with chloroform. The organic phase is washed with $H_2O$, dried and evaporated, to give 13 g of the desired compound (19.3 mmol).

Yield: 39%
Elemental analysis

| | C | H | N |
|---|---|---|---|
| % calc.: | 56.95 | 8.66 | 8.30 |
| % found: | 56.67 | 8.68 | 8.30 |
| TLC: | silica gel plate 60F 254 Merck | | |
| Eluent: | $CHCl_3$/MeOH/$NH_4OH$ 25% = 6:3:1 | | |
| | Rf = 0.65 | | |
| Detection: | $KMnO_4$ in alkaline solution | | |

The $^1$H-NMR, $^{13}$C-NMR, IR and MS spectra are consistent with the indicated structure.

B) (3β,5β,7α,12α)-3-[[[[[Bis[2-[bis[2-(1,1-dimethylethoxy)-2-oxoethyl]amino]ethyl]amino]acetyl] amino]acetyl]amino]-7,12-dihydroxycholan-24-oic acid methyl ester 2.8 mL of TEA (20.2 mmol) are dropwise added in 5 min to a solution of 13.6 g of the compound prepared at step A) (20.2 mmol), 8.52 g of (3β,5β,7α,12α)-3-amino-7,12-dihydroxycholan-24-oic acid methyl ester (prepared in Example 5) (20.2 mmol) and DEPC (3.4 mL; 22.2 mmol) in DMF (290 ml) stirring at 0° C. After 1 h the reaction is warmed to room temperature and the solution is stirred for 6.5 h. 0.3 mL of DEPC (2 mmol) are added and the solution is stirred for a further 15.5 h. DMF is evaporated off, the residue is dissolved in EtOAc, washed with aq. $NaHCO_3$ and then water and finally dried. Purification by flash chromatography yields 13.7 g of the desired product (12.7 mmol).

Yield: 63%
$[\alpha]_D^{20}$ = +5.26 (c 1.5; $CHCl_3$)
Elemental analysis

| | C | H | N |
|---|---|---|---|
| % calc.: | 63.48 | 9.25 | 6.49 |
| % found: | 63.22 | 9.40 | 6.40 |

The $^1$H-NMR, $^{13}$C-NMR, IR and MS spectra are consistent with the indicated structure.

C) (3β,5β,7α,12α)-3-[[[[[Bis[2-[bis(carboxymethyl)amino] ethyl]-amino]acetyl]amino]acetyl]amino]-7,12-dihydroxycholan-24-oic acid 12.85 g of the compound prepared at step B) (12 mmol) are dissolved in TFA (210 mL) stirring at 0≈5° C. After 16 h TFA is evaporated off to give a residue which is dissolved in 90 mL of 0.8M NaOH at pH 13 and stirred at room temperature for 15 h. The solution is concentrated to 50 mL, dropped in 105 mL of 0.6M HCl and stirred for 2 h. The solid is filtered, washed with 0.1M HCl and dried to obtain a crude which is purified by chromatography. The fractions containing the desired compound in salified form are evaporated to give a residue which is dissolved in water and dropped into 1M HCl at pH 1.45. The precipitate is filtered, washed with 0.1M HCl and dried to give 2.6 g of the desired product (3.1 mmol).

Yield: 26% m.p.: 120–125° C.
HPLC assay: 98% (area %)
The $^1$H-NMR, $^{13}$C-NMR, IR and MS spectra are consistent with the indicated structure.

Example 8

Preparation of Cholic Acid Derivative Chelating Agents

Using (3β,5β,7α,12α)-3-amino-7,12-dihydroxycholan-24-oic acid methyl ester prepared as described in Example 5, and following the procedures described in WO-A-95/32741, the following chelating agents were prepared:

[3β(S),5β,7α,12α]-3-[[4-[bis[2-[bis(carboxymethyl)amino] ethyl]-amino]-4-carboxy-1-oxobutyl]amino]-7,12-dihydroxycholan-24-oic acid;

[3β(S),5β,7α,12α]-3-[[4-[[5-[bis[2-[bis(carboxymethyl) amino]-ethyl]amino]-5-carboxypentyl]amino]-1,4-dioxobutyl]amino]-7,12-dihydroxycholan-24-oic acid;

(3β,5β,7α,12α)-3-[[[[bis[2-[bis(carboxymethyl)amino] ethyl]amino]acetyl]amino]acetyl]amino]-7,12-dihydroxycholan-24-oic acid;

(3β,5β,7α,12α)-3-[[6-[[[bis[2-[bis(carboxymethyl)amino] ethyl]amino]acetyl]amino]-1-oxohexyl]amino]-7,12-dihydroxycholan-24-oic acid;

(3β,5β,7α,12α)-3-[[N-[N-[2-[[2-[bis(carboxymethyl) amino]ethyl]-(carboxymethyl)amino]ethyl]-N-(carboxymethyl)glycyl]glycyl]amino]-7,12-dihydroxycholan-24-oic acid;

18-[[(3β,5β,7α,12α)-23-carboxy-7,12-hydroxy-24-norcholan-3-yl]amino]-3,6,9-tris(carboxymethyl)-11,18-dioxo-3,6,9,12-tetraazaoctadecanoic acid.

What is claimed is:

1. (3β,5β,12α)-12-hydroxy-3-[[(2-hydroxymethyl) benzoyl]amino]cholan-24-oic acid methyl ester of formula (IVc)

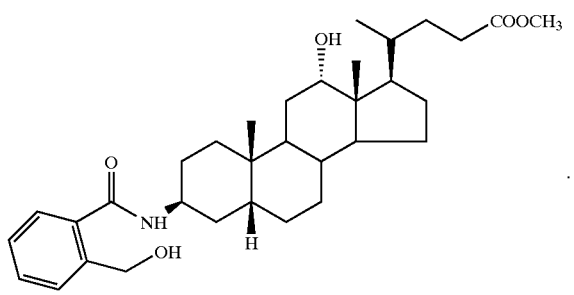

(IVc)

* * * * *